(12) United States Patent
Ascione et al.

(10) Patent No.: US 11,591,587 B2
(45) Date of Patent: Feb. 28, 2023

(54) PROCESS FOR PLASMINOGEN PURIFICATION STARTING FROM HUMAN PLASMA

(71) Applicant: KEDRION S.P.A., Barga (IT)

(72) Inventors: Ester Ascione, Santa Maria Capua Vetere (IT); Claudio Farina, Pisa (IT); Alessandra Lazzarotti, Gallicano (IT); Marcella Maddaluno, Lucca (IT); Claudia Nardini, Lucca (IT)

(73) Assignee: KEDRION S.P.A., Barga (IT)

( * ) Notice: Subject to any disclaimer, the term of this patent is extended or adjusted under 35 U.S.C. 154(b) by 0 days.

(21) Appl. No.: 16/333,023

(22) PCT Filed: Sep. 12, 2017

(86) PCT No.: PCT/EP2017/072824
§ 371 (c)(1),
(2) Date: Mar. 13, 2019

(87) PCT Pub. No.: WO2018/050618
PCT Pub. Date: Mar. 22, 2018

(65) Prior Publication Data
US 2019/0330611 A1    Oct. 31, 2019

(30) Foreign Application Priority Data

Sep. 13, 2016    (IT) .................. 102016000091964

(51) Int. Cl.
*C12N 9/68*    (2006.01)
(52) U.S. Cl.
CPC .... *C12N 9/6435* (2013.01); *C12Y 304/21007* (2013.01)

(58) Field of Classification Search
None
See application file for complete search history.

(56) References Cited

U.S. PATENT DOCUMENTS

2004/0171103 A1    9/2004    Bradley et al.

FOREIGN PATENT DOCUMENTS

| EP | 0638314 A1 | 2/1995 |
| WO | 2002/095019 A1 | 11/2002 |

OTHER PUBLICATIONS

Chibber, B.A.K., et al. 1974 Methods in Enzymology 34: 424-432. (Year: 1974).*
Deutsch, D.G., et al. 1970 Science 170(3962): 1095-1096. (Year: 1970).*
Liumbruno, G.M., et al. 2015 J Thromb Thrombolysis 39: 118-128. (Year: 2015).*
International Search Report and Written Opinion for corresponding Application No. PCT/EP2017/072824 (dated Dec. 12, 2017).

* cited by examiner

*Primary Examiner* — Marsha Tsay
(74) *Attorney, Agent, or Firm* — Troutman Pepper Hamilton Sanders LLP (Rochester)

(57) ABSTRACT

The present invention provides a process for the production of human plasminogen starting from human plasma or a fractionation intermediate thereof. The main stages of the process are: a step of virus inactivation, in which human plasma is contacted with a solvent/detergent mixture, a single affinity chromatographic step and a virus removal nanofiltration step. This process is scalable up to industrial level and it provides, without adding any protease inhibitor, a functional and intact finished product suitable to be administered for the treatment of human diseases due to genetic plasminogen deficiency.

7 Claims, 4 Drawing Sheets

PROCESS FOR PLASMINOGEN PURIFICATION STARTING FROM HUMAN PLASMA

FIELD OF THE INVENTION

The present invention relates to the field of blood products, in particular to purification and production of human plasminogen.

STATE OF THE ART

Plasminogen (Pg) is synthetized as a plasma zymogen and is converted to the serine protease Plasmin (Pm) by the physiological activators urokinase (uPA) or tissue plasminogen activator (tPA), causing the activation of the fibrinolytic system. Indeed, the primary in vivo function of Pm is to regulate vascular potency by degrading fibrin-containing thrombi.

The primary tissue that synthesizes plasminogen is the liver, however other sources have been identified; they include adrenal glands, kidneys, brain, testis, heart, lung, uterus, spleen, thymus, and gut. Plasminogen is synthesized as a 810-amino acids polypeptide; its native form has a $NH_2$-terminal glutamic acid and it is called Glu-Pg. The mature form of plasminogen (791-amino acids) is due to cleavage of a 19-amino acid leader peptide during the secretion. The conversion of human plasminogen to plasmin involves cleavage of $Arg^{561}$-$Val^{562}$ bond resulting in the generation of Glu-Pm, which contains a N-terminal heavy chain of 561-amino acids and a disulfide-linked carboxy-terminal light chain of 230-amino acids. Plasmin catalyzes the hydrolysis of the N-terminal $Glu^1$-Pg in position 77, converting $Glu^1$-Pg to another plasminogen form called $Lys^{76}$-Pg. This conversion is important for maximal enhancement in Glu-Pg activation on cell surface.

The first documented abnormal human plasminogen was reported over 25 years ago in a patient heterozygous for a plasminogen deficiency with a history of thrombotic events. Homozygous or compound heterozygous mutations in plasminogen gene trigger a severe inflammation threatening visual function when affecting the cornea named ligneous conjunctivitis or pseudomembranous disease and, in some cases, occlusive hydrocephalus.

Several methods relative to plasminogen purification have previously been described.

Deutsch D. G. and Mertz E. (Science 1970, 170, 1095-1096) describe a method of plasminogen purification from human plasma based on affinity chromatography using Lysine-Sepharose 4B resin. A volume of 340 mL of plasma (diluted to 640 mL with water) was passed through 150 mL of resin, washed with 0.3 M phosphate buffer and 3 mM EDTA, and the elution of plasminogen was conducted with 0.2 M ε-aminocaproic acid which was removed, in the cold, by means of Sephadex G-25 column.

Grant A. J. (Biochem. Int. 1990, 20(3), 519-527) describes a method based on double affinity chromatography, in conditions similar to Deutsch and Mertz. The process was carried out at 4° C., by adding protease inhibitors in each purification step, in order to prevent spontaneous activation of plasminogen to plasmin by activators present in the plasma.

U.S. Pat. No. 3,943,245 describes the purification of plasminogen from human and non-human mammalian plasma or Cohn Fraction III by modified affinity chromatography using Sepharose-L-lysine with high ionic strength buffer solutions as in ion exchange chromatography.

EP0638314 describes the purification of plasminogen starting from Cohn's fraction II+III subjecting it to solvent/detergent (S/D) viral inactivation step before the affinity chromatography step on a lysine-Sepharose column which was washed with 0.9% glycine solution (pH 7.2) containing 0.9% sodium chloride and 500 mL of 0.9% glycine solution (pH 7.2) containing 1 M sodium chloride and elution of adsorbed plasminogen was carried out with 0.9% glycine solution (pH 7.2) containing 0.25 M lysine. The thus lyophilized plasminogen preparation was subjected to a dry heat treatment at 60° C. to 80° C. for 72 hours or more to produce a Lys type plasminogen-containing composition in which viruses were removed or inactivated.

The aim of the invention is to provide a process scalable to industrial level for obtaining a purified and virus safe plasminogen suitable to be administered to humans for therapeutic purposes.

SUMMARY OF THE INVENTION

Subject-matter of the present invention is a process of purification of plasminogen starting from human plasma or a fractionation intermediate thereof; said process comprising:
ii) a step of virus inactivation in which human plasma is contacted with a solvent/detergent mixture;
v) a single affinity chromatographic step on L-lysine immobilized cross-linked agarose resin; and
ix) a virus removal nanofiltration step;
wherein said virus inactivation (ii) is performed upstream the affinity chromatography and said nanofiltration (ix) is performed downstream the affinity chromatography.

In order to ensure a finished product suitable for therapy in humans, besides the solvent/detergent treatment (ii), that ensures a product safe from enveloped viruses, the present invention also includes a nanofiltration step (ix) which protects the preparation from small enveloped and non-enveloped viruses, such as for example HAV.

The process of the present invention does not require any addition of protease inhibitors. As previously reported, traditional processes for purification of plasminogen suggest the use of protease inhibitors (eg. aprotinin, PMSF and soybean trypsin inhibitor) to prevent spontaneous activation of plasminogen to plasmin by activators being in plasma. In the present method, on the contrary, no preservative agents are added and a fully functional plasminogen is obtained in total absence of any protease inhibitors.

In accordance with the present invention, a virally inactivated and highly pure plasminogen preparation is obtained starting from human plasma or from a fractionation intermediate thereof. The purification method here described is efficient, reproducible and scalable up to industrial level, allowing to produce functional and intact Glu-plasminogen without adding any protease inhibitor as preservative agent.

Thanks to the specific interactions between the resin and the target protein, the present invention provides a single chromatography based method, sufficient to obtain a highly pure plasminogen preparation. The high level of purity makes such plasminogen composition suitable for use in the treatment of human diseases due to genetic plasminogen deficiency.

DETAILED DESCRIPTION OF THE INVENTION

The block outline of the method of the invention is fully described in FIG. 1. According to the invention, starting material can be human plasma or fractionation intermediates thereof wherein fractionation intermediates means cryoprecipitate, Cohn Fraction III or Cohn Fraction II+III. According to one particular and preferred aspect, the starting material for plasminogen purification is a frozen source of plasma. Preferably, in the initial step of the production the human frozen plasma is thawed under continuous stirring until a temperature of 20±1° C. is reached and the pH is adjusted to 7.0-8.0 with pressurized $CO_2$ or $N_2$. According to the invention, the thawed plasma is preferably clarified by a filtration step (i) on a 1 μm filter and subsequently it is submitted to the viral inactivation step (ii) contacting the solution with a mixture of solvent/detergent (S/D). This step (ii) envisages ensuring a finished product safe from enveloped viruses. For one preferred aspect the S/D mixture has the following composition: 1% w/w Triton X-100 and 1% w/w tri-(n-butyl)-phosphate (TnBP). Preferably, the mixture is added to the plasma at a 30° C.±1° C. and stirred for 30 minutes. The S/D treatment is carried out for at least six hours at 28° C.±1° C.; during the treatment, the pH is monitored and eventually is adjusted to 7.0-8.0.

In order to facilitate the separation of the S/D mixture from plasma, at the end of the viral inactivation step (ii), Castor Oil addition step (iii) is preferably included. In a preferred embodiment, Castor Oil concentration is 3-5% of S/D plasma; it is added at 20° C.±1° C. and stirred for 60 minutes, then the solution is kept at rest for at least 1 hour with the purpose of separating the S/D phase from plasma phase. The addition of Castor Oil envisages an improvement of the plasma filterability, reducing the risk of loading S/D onto the column during the following chromatography, thus preserving the integrity of the resin.

At the end of the afore mentioned step (iii), plasma is preferably subjected to a filtration step (iv) and thus filtered through a 3.00-0.5 μm depth filter.

The subsequent affinity chromatography step (v) is preferably performed on the affinity resin ECH-Lysine Sepharose 4 Fast Flow which is based on a highly cross-linked 4% agarose and enables rapid processing of large sample volumes. Differently from the previously used Lysine Sepharose 4B, not suitable for industrial production of plasminogen, the ECH-Lysine Sepharose 4 Fast Flow resin can be submitted to several cleaning cycles with many commonly used agents, thus ensuring the safety of the finished product with no impact on integrity and functionality of the resin itself, also at an industrial level.

The advantage of using ECH-Lysine Sepharose 4 Fast Flow is that said resin is based on a highly cross-linked 4% agarose, thus enabling rapid processing of large sample volumes appropriate to industrial production. The stable ether linkage, that covalently binds the L-Lysine to a long hydrophilic spacer arm (see Scheme 1) attached on Sepharose 4 Fast Flow, also permits to submit the resin to several cleaning cycles without losing its integrity and functionality.

Being the plasminogen designed to be administered in humans, the cleaning of the resin, after each production, is essential for the safety of the finished product and it avoids cross-contamination. In this regard, the affinity chromatography described in the present invention represents an improvement of the previously used Lysine Sepharose 4B resin whose documented instability to the cleaning agents, makes said resin not suitable for industrial production of plasminogen. Long term stability studies showed that ECH-Lysine Sepharose 4 Fast Flow can be treated with many commonly used cleaning agents without any significant changes neither in ligand concentration nor in plasminogen binding capacity, the exception being long exposure under strongly basic conditions.

For the industrial scalability of the method, high binding capacity of the resin is important, in order to maximize the yield of the finished product. As shown in the experimental section, up to 38 column volumes (CV) of inactivated plasma can be loaded onto the ECH-Lysine Sepharose 4 Fast Flow resin. Therefore, in a preferred embodiment, 30-35 CV represent the optimal loading volume to obtain high plasminogen yield, avoiding resin saturation. According to one particular aspect, the starting material is loaded onto the column at 150-250 cm/h linear flow rate with pressure values 0.1 MPa. Lower flow rate values entail long loading time, certainly not suitable for the industrial scale up of the method. In a preferred embodiment, the buffer used for affinity chromatography on ECH-Lysine Sepharose 4 Fast Flow resin are the following:

sodium phosphate 0.05 M, sodium chloride 0.1 M, pH 7.4 for resin equilibration;
sodium phosphate 0.05 M, sodium chloride 0.1 M pH 7.4 for resin washing;
sodium phosphate 0.05 M, ε-aminocaproic acid 0.05 M, sodium chloride 0.1 M pH 7.4 for plasminogen elution.

As shown in the experimental section, the above buffers (i.e. buffer composition B) used in the affinity chromatography step (v), compared with the other tested buffers (i.e. buffer composition A), allow to obtain a higher plasminogen yield.

In order to remove particulates, the chromatographic product of step (v) is preferably subjected to a filtration step (vi) through a 0.22 μm filter, then the plasminogen purification preferably prosecutes with an ultrafiltration step (vii), making it possible to obtain a concentrated and dialyzed protein solution suitable for ocular administration. In particular, ultrafiltration (vii) is performed with 20-25 volumes of saline solution (0.1 M sodium chloride) by using 30,000 Dalton dialysis cassettes to remove ε-aminocaproic acid; then the system is washed with 0.1 M sodium chloride to achieve a 0.7÷1.3 mg/mL protein concentration.

After adjusting the pH to 7.1±0.7, the plasminogen solution is preferably subjected to a filtration step (viii) through a 0.1 μm filter and subsequently subjected to the viral Scheme 1 - Partial structure of ECH-Lysine Sepharose 4 fast Flow

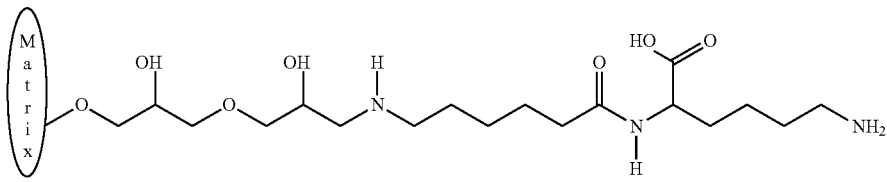

removal step (ix), namely nanofiltration. For one preferred aspect, nanofiltration (ix) involves filtration through a 20 nanometer viral grade filter. The preparation is then preferably submitted to a sterile filtration through a 0.22 μm filter (x) and the plasminogen bulk thus obtained is preserved at the temperature≤−20° C.

Besides the solvent/detergent treatment (ii) that ensures a product safe from enveloped viruses, the nanofiltration step (ix) protects from small enveloped and non-enveloped viruses, such as for example HAV. This virus removal procedure certainly allows an improvement of the plasminogen purification process compared to what has previously been described in literature.

As reported by Grant, traditional purification processes suggest the use of protease inhibitors (eg. aprotinin, PMSF and soybean trypsin inhibitor), in order to ensure plasminogen integrity in the finished product and to prevent its activation. The present method, on the contrary, allows to obtain a fully functional plasminogen without adding any preservative agent, thus avoiding adverse effects thereof. Plasminogen totally preserves its integrity and, as shown in the experimental section, comparability study between plasminogen obtained with or without aprotinin demonstrates that there are no differences neither in plasminogen antigen nor in activity and yield thereof.

For another preferred aspect, plasminogen preparation herein described is mainly in the form of Glu-Pg, which represents the dominant form of plasminogen in plasma. The circulating half-life of Glu-Pg is greatly higher than Lys-Pg, thus the present invention provides a method to obtain plasminogen preparation suitable for therapy in humans.

Further description details are provided in the following examples. Said examples are useful for clarifying the method and do not limit it in anyway.

EXPERIMENTAL SECTION

Example 1—Resin Binding Capacity in Terms of Column Volumes (CV)

One of the most important aspects of a chromatography scalable up to industrial level is a high binding capacity, with the aim of maximizing yield, without altering the functionality of the product.

Figure 1:
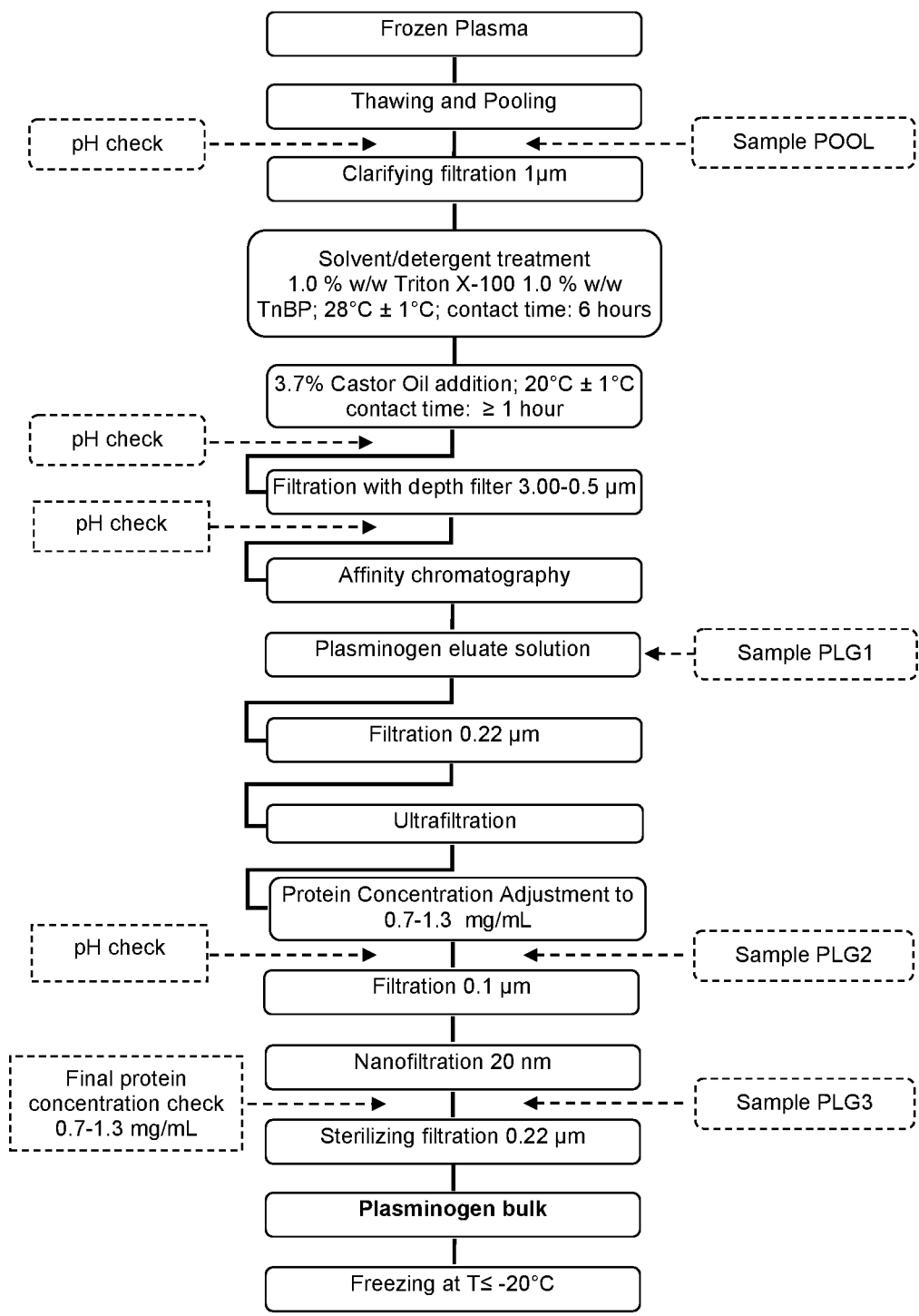
FIG. 1 shows the block outline of one preferred embodiment of the process of the invention, from the raw material to attainment of plasminogen finished product.
Figure 2:
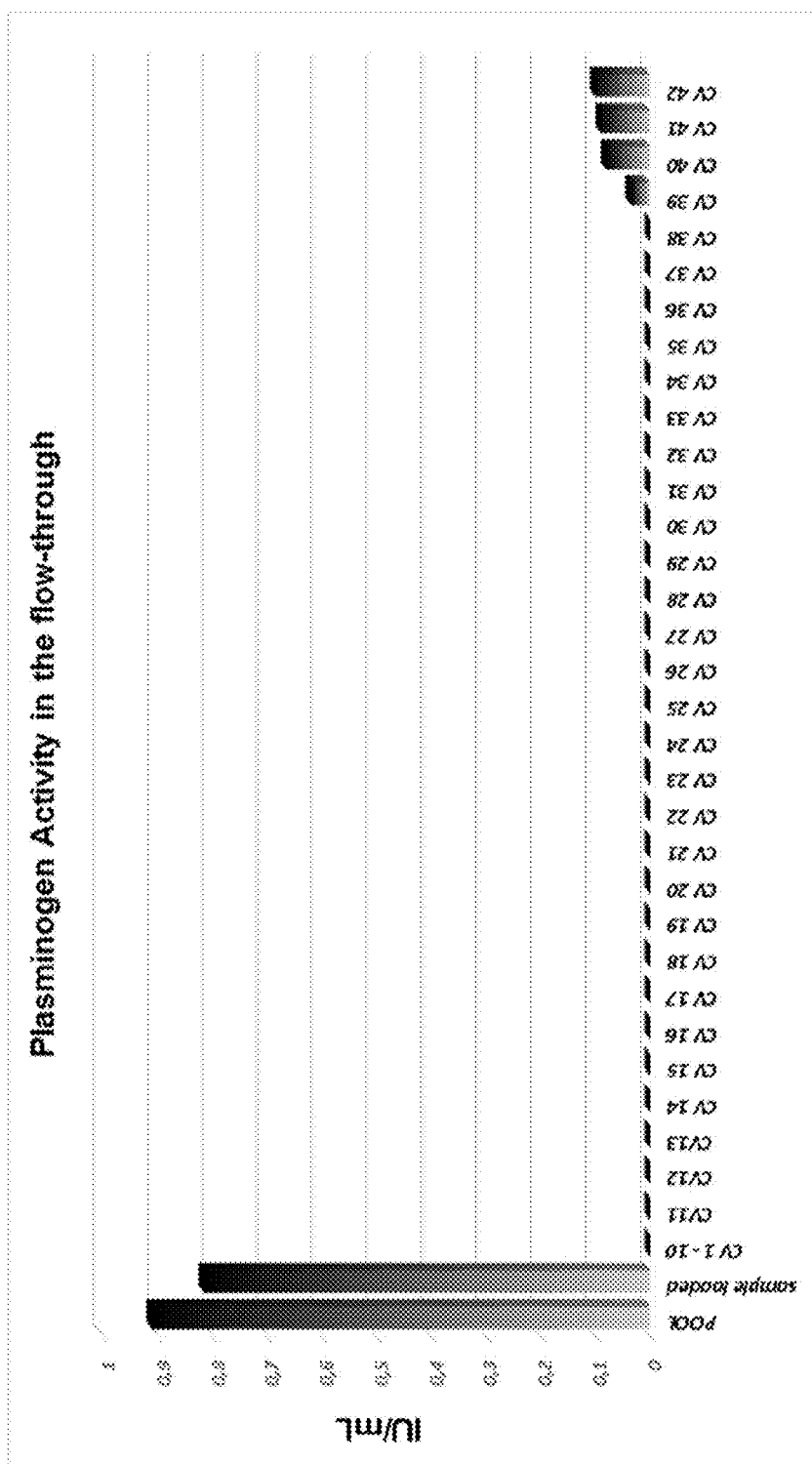
FIG. 2 shows the maximum binding capacity, in terms of Column Volumes (CV), of the ECH-Lysine Sepharose 4 Fast Flow resin. Plasminogen Activity was evaluated in the flow-through until it reached at least 10% of the original activity found in pool plasma.

In order to identify the maximum binding capacity of the ECH-Lysine Sepharose 4 Fast Flow (packed into a column 16 mm of diameter by 15±1 cm of height, wherein 1 CV was 30 mL), 1.3 Kg of S/D plasma, subjected to Castor Oil addition and then filtered through a 3.00-0.5 μm depth filter, were loaded onto such resin at 50 cm/h; plasminogen activity in the flow-through (FT) was analyzed until it reached at least 10% of the original activity found in pool-plasma. As shown in FIG. 2, no plasminogen activity was observed in the FT up to 38 CV, while it was registered starting from 39 CV. Experiments performed loading 10 or 32 CV demonstrated that any significant differences were found neither in terms of plasminogen antigen nor in terms of activity in the elution fraction, namely PLG1 (Table 1). Therefore the binding capacity of the ECH-Lysine Sepharose 4 Fast Flow was established to be 38 CV, however the loading volume, ensuring high plasminogen yield and avoiding resin saturation, was set between 30 and 35 CV. According to this experiment it resulted a binding capacity between 3 and 3.5 mg plasminogen/mL drained resin.

Example 2—Loading and Elution Conditions Optimization

The loading sample step of chromatography was initially performed at 50 cm/h. Such flow rate, for high loading volume (30-35 CV), entails long duration time of chromatography, not suitable for industrial processes. In this regard, the loading flow rate was increased up to 200 cm/h, maintaining low back pressure, thus reducing the step duration from 7 hours to less than 2 hours. In this condition, a decrease of the plasminogen yield from 80.35% to 70% was observed (Table 1) thus further optimizations, regarding the composition of the buffers, have needed to be investigated.

Figure 3:
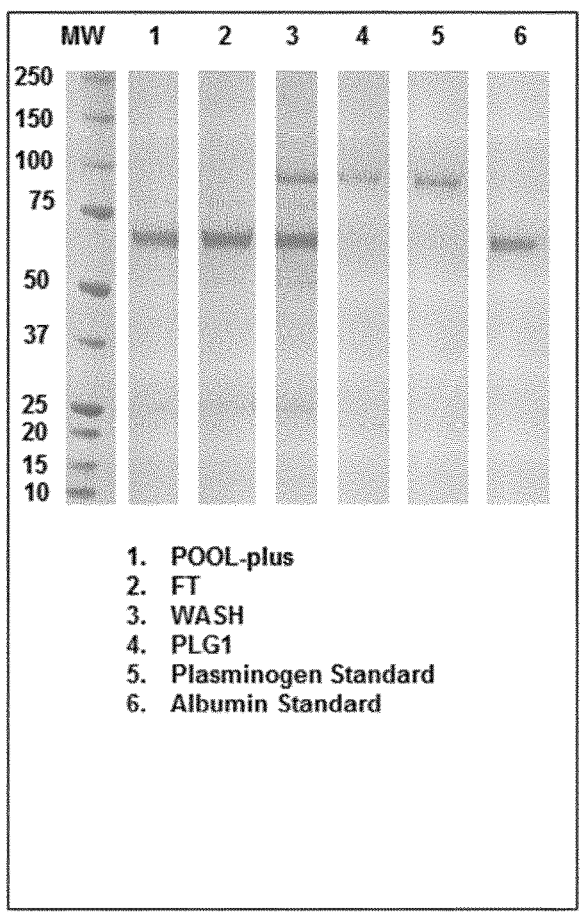
FIG. 3 shows representative SDS-PAGE of chromatographic step performed by means of buffer composition A vs buffer composition B as reported in table 2.
Figure 3:
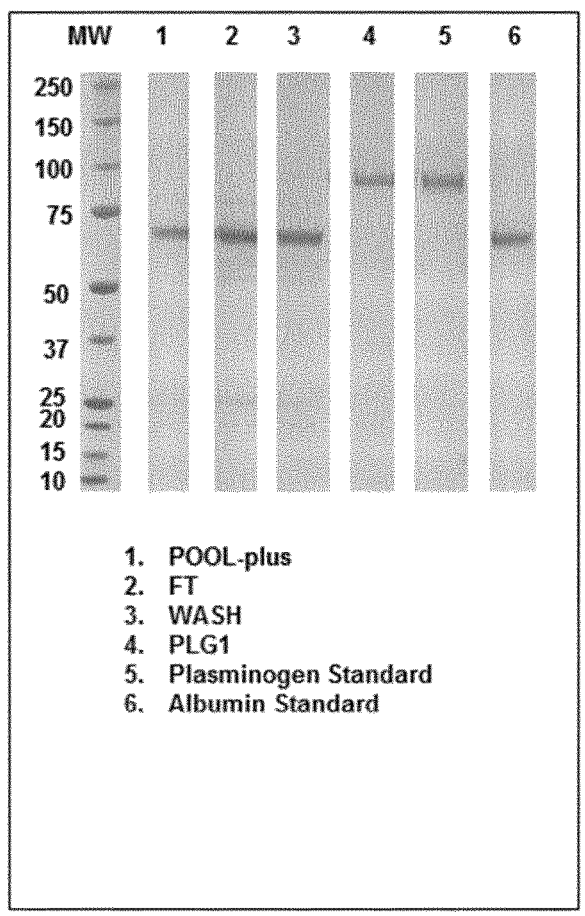

Composition of the buffers used at the beginning, namely composition A, was substituted with composition B, which mainly differed for absence of EDTA (Table 2); loading volume and flow rate were unchanged. As shown in Table 1, using buffer composition B decreased the loss of plasminogen in the washing fraction and, at the same time, it significantly improved the plasminogen yield in the elution fraction up to 90.40%. This result was confirmed by Sodium Dodecyl Sulphate PolyAcrylamide Gel Electrophoresis (SDS-PAGE) analysis (FIG. 3): the washing step performed with buffer composition A showed a band corresponding to plasminogen molecular weight, demonstrating the loss of plasminogen during this step; such band was not visible in case of washing step performed with buffer composition B. Furthermore, buffer composition B significantly increased the removal of the main contaminant albumin in the washing step, thus reducing the content thereof in the elution fraction (Table 1).

The optimized chromatographic conditions were the following: 30-35 CV loading volume; 200 cm/h flow rate; buffer composition B.

TABLE 1

Chromatography performed in different conditions of loading volumes, flow rates, buffers composition, presence or absence of aprotinin. Results are expressed as mean ± SD from three separate experiments run in triplicate

| Buffer | CV | Flow rate | SAMPLE | PLG (IU/mL) Mean | SD | PLG (g/L) Mean | SD | Albumin (g/L) Mean | SD | PLG Yield |
|---|---|---|---|---|---|---|---|---|---|---|
| PURIFICATION IN PRESENCE OF APROTININ ||||||||||||
| A | 10 | 50 cm/h | Pool Plasma | 0.91 | 0.01 | 0.12 | 0.01 | 32 | 0.14 | 80.50 ± 6.0% |
|   |   |   | FT | — | — | — | — | 28.55 | 0.07 |   |
|   |   |   | WASH | — | — | — | — | 0.023 | 0.0019 |   |
|   |   |   | PLG1 | 11.62 | 0.01 | 1.49 | 0.02 | 0.009 | 0.0001 |   |
| PURIFICATION IN PRESENCE OF APROTININ ||||||||||||
| A | 32 | 50 cm/h | Pool Plasma | 0.82 | 0.01 | 0.11 | 0.01 | 34.75 | 0.21 | 80.35 ± 5.5% |
|   |   |   | FT | — | — | — | — | 34.5 | 1.6 |   |
|   |   |   | WASH | 0.1 | 0.01 | 0.01 | 0 | 0.266 | 0.0028 |   |
|   |   |   | PLG1 | 14.14 | 0.2 | 1.78 | 0.03 | 0.012 | 0.0003 |   |
| PURIFICATION IN PRESENCE OF APROTININ ||||||||||||
| A | 32 | 200 cm/h | Pool Plasma | 0.9 | 0.01 | 0.11 | 0 | 31.5 | 0 | 70.00 ± 5.1% |
|   |   |   | FT | — | — | — | — | 31.65 | 0.49 |   |
|   |   |   | WASH | 0.33 | 0.01 | 0.03 | 0 | 0.084 | 0.0022 |   |
|   |   |   | PLG1 | 12.46 | 0.2 | 1.38 | 0.01 | 0.008 | 0.0002 |   |
| PURIFICATION IN PRESENCE OF APROTININ ||||||||||||
| B | 32 | 200 cm/h | Pool Plasma | 0.88 | 0.02 | 0.11 | 0 | 35.3 | 0.14 | 90.40 ± 6.2% |
|   |   |   | FT | — | — | — | — | 34.3 | 0.28 |   |
|   |   |   | WASH | 0.14 | 0.01 | 0.01 | 0 | 0.561 | 0.0014 |   |
|   |   |   | PLG1 | 18.48 | 0 | 2.1 | 0 | — | — | — |
| PURIFICATION IN ABSENCE OF APROTININ ||||||||||||
| B | 32 | 200 cm/h | Pool Plasma | 0.85 | 0.01 | 0.1 | 0 | 35.6 | 0.57 | 88.00 ± 5.8% |
|   |   |   | FT | — | — | — | — | 34.2 | 0.14 |   |
|   |   |   | WASH | 0.08 | 0 | — | — | 0.431 | 0.0014 |   |
|   |   |   | PLG1 | 15.54 | 0.2 | 1.65 | 0.02 | 0.004 | 0.00004 |   |

TABLE 2

Two different chromatographic buffers composition, namely composition A and composition B.

| Chromatographic Step | Buffer | Buffer Composition A | Buffer Composition B |
|---|---|---|---|
| Conditioning | 1 | Sodium phosphate 0.05M, EDTA 0.003M, pH 7.4 | Sodium phosphate 0.05M, sodium chloride 0.1M, pH 7.4 |
| Washing | 2 | Sodium phosphate 0.05M, sodium chloride 0.4M, EDTA 0.003M, pH 7.4 | Sodium phosphate 0.05M, sodium chloride 0.1M, pH 7.4 |
| Elution | 3 | Sodium phosphate 0.05M, ε-aminocaproic acid 0.2M, pH 7.4 | Sodium phosphate 0.05M, ε-aminocaproic acid 0.05M, sodium chloride 0.1M, pH 7.4 |

Example 3—Presence or Absence of a Protease Inhibitor

Figure 4:
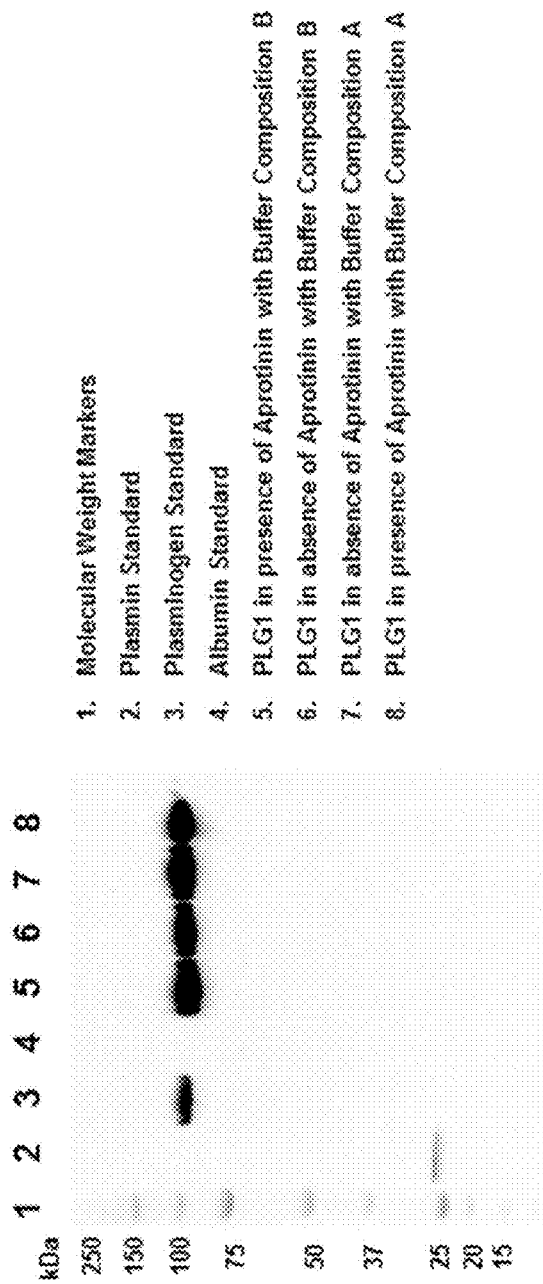
FIG. 4 shows representative Western Blot of plasminogen obtained in presence or absence of aprotinin by means of chromatography buffer composition A vs buffer composition B.

In order to establish if the method allowed obtaining a fully functional plasminogen in absence of any preservative agent, such as protease inhibitors, the purification was carried out both with and without adding bovine aprotinin (20 KIU/mL) to the thawed plasma before performing the 1 μm clarifying filtration. As shown in Table 1, the absence of aprotinin did not change plasminogen antigen, activity and yield; moreover, although an increase of the albumin content in the elution fraction was observed, it was not significant. FIG. 4 shows the results obtained from Western Blot analysis relative to chromatography performed in presence or absence of aprotinin by means of buffer composition A vs buffer composition B: none of the analyzed samples showed the activation band corresponding to plasmin demonstrating that, even in absence of aprotinin, plasminogen totally preserved its integrity.

Example 4—ELISA for Glu-Pg

It is well known that the half-life of Glu-Pg circulating in plasma is greatly higher than the other plasminogen form called Lys-Pg. In order to investigate the form of plasminogen obtained in the present invention, enzyme linked immunosorbent assay (ELISA) was performed on finished product by means of a specific antibody able to recognize only the Glu-Pg form. As shown in Table 3, such experiments demonstrated that the chromatographic purification performed with Buffer Composition B, both in presence and absence of aprotinin, provided a finished product whereof more than 98% of plasminogen was in the form of Glu-Pg.

TABLE 3

ELISA for Glu-PLG. Results are expressed as mean ±
SD from three separate experiments run in triplicate

| | Pg (mg/mL) | | Glu-Pg (mg/mL) | | |
|---|---|---|---|---|---|
| Sample Description | Mean | SD | Mean | SD | Glu-Pg/Pg |
| PLG with Buffer Composition A | 1.38 | 0.01 | 1.24 | 0.12 | 89.8% |
| PLG with Buffer Composition B | 2.10 | 0.00 | 2.07 | 0.15 | 98.6% |
| PLG with Buffer Composition B in absence of aprotinin | 1.65 | 0.02 | 1.70 | 0.05 | 103.0% |

Example 5—Best Embodiment of the Process

Human frozen plasma (1.88 Kg) was thawed under continuous stirring until the temperature reached 20° C. pH was adjusted to 7.5 with $CO_2$ and, after filtration on a 1 μm filter, 1.74 Kg of thawed plasma were subjected to the viral inactivation step: the S/D mixture, composed of 1% w/w Triton X-100 (17.44 g) and 1% w/w TnBP (17.44 g), was added at a 30° C. and stirred for 30 minutes. The S/D treatment was carried out for six hours at 28° C. and, at the end of this time, 65.8 g of Castor Oil (3.7% of S/D plasma) were added at 20° C. under stirred condition for 60 minutes; then the solution was kept at rest for 1 hour in order to separate the S/D phase from plasma phase. After filtration through a 3.00-0.5 μm depth filter, 1.0 Kg of S/D plasma was loaded on the affinity resin ECH-Lysine Sepharose 4 Fast Flow (packed into a column 16 mm of diameter by 15 cm of height). The amount of plasma loaded corresponded to 33 CV; the linear flow rate was 200 cm/h and buffers used were the same as described in Table 2 (buffer composition B).

The chromatographic product (0.035 Kg) was filtered through a 0.22 μm filter and, in order to remove ε-aminocaproic acid, ultrafiltration was performed with 20-25 volumes of saline solution (0.1 M sodium chloride) by using 30,000 Dalton dialysis cassettes. After that, the system was washed with 0.1 M sodium chloride solution adjusting the protein concentration to 1.2 mg/mL, and the plasminogen solution thus obtained (0.07 Kg), was filtered by using a 0.1 μm filter. Subsequently the viral removal step was performed by passing the solution through a 20 nanometer viral grade nanofilter Planova 20N and, after a final sterile filtration, the plasminogen bulk preparation (0.07 Kg) was preserved at the temperature–20° C. More than 98% portion of plasminogen obtained was Glu-Pg.

The invention claimed is:

1. An industrial scale process for obtaining a highly purified and virus safe plasminogen (Pg) containing more than 98% wt native form plasminogen (Glu-Pg) suitable to be administered to humans for therapeutic purposes, said process starting from frozen human plasma; said process comprising:
   contacting the frozen human plasma thawed at 20±1° C. with a solvent/detergent mixture for virus inactivation;
   subjecting the human plasma, after said virus inactivation, to a single affinity chromatographic step on L-lysine immobilized cross-linked agarose resin wherein the affinity chromatography resin is ECH-Lysine SEPHAROSE® 4 Fast Flow and wherein the buffers used for affinity chromatography on ECH-Lysine SEPHAROSE® 4 Fast Flow resin are the following:
   sodium phosphate 0.05 M, sodium chloride 0.1 M, pH 7.4 for resin equilibration;
   sodium phosphate 0.05 M, sodium chloride 0.1 M pH 7.4 for resin washing;
   sodium phosphate 0.05 M, ε-aminocaproic acid 0.05 M, sodium chloride 0.1 M pH 7.4 for plasminogen elution to obtain a native form plasminogen eluate; and
   nanofiltering the native form plasminogen eluate from said affinity chromatographic step through a nanofilter to remove viral contaminants wherein filtrate from said nanofiltering step comprises purified and virus safe plasminogen (Pg) containing more than 98% wt native form of plasminogen (Glu-Pg) suitable to be administered to humans for therapeutic purposes, and wherein no protease inhibitor is employed during said process.

2. The process according to claim 1, further comprising adding castor oil to the human plasma after said virus inactivation step and before said affinity chromatography step.

3. The process according to claim 1, further comprising an ultrafiltering step which is performed after said affinity chromatographic step and before said nanofiltering step.

4. The process according to claim 1, wherein the solvent detergent mixture used in the virus inactivation step has the following composition: 1% w/w TRITON® X-100 and 1% w/w tri-(n-butyl)-phosphate (TnBP).

5. The process according to claim 1, wherein the nanofilter is a 20 nanometer viral grade filter.

6. The process of claim 1 further comprising filtering the eluate through a dialysis membrane with a 0.1M NaCl solution to remove ε-aminocaproic acid.

7. An industrial scale process for obtaining a highly purified and virus safe plasminogen (Pg) containing more than 98% wt native form plasminogen (Glu-Pg) suitable to be administered to humans for therapeutic purposes, said process starting from frozen human plasma; said process consisting of the following steps performed in sequence:
   filtering human plasma thawed at 20±1° C. on a 1 μm filter;
   contacting the filtered human plasma with a solvent/detergent mixture to inactivate viruses;
   adding castor oil to the virus inactivated human plasma to form a mixture;
   filtering the mixture through a 3.00-0.5 μm depth filter to obtain a filtrate of virus inactivated human plasma;
   subjecting the virus inactivated human plasma filtrate to a single affinity chromatography using a L-lysine immobilized cross-linked agarose resin wherein the affinity chromatography resin is ECH-Lysine SEPHAROSE® 4 Fast Flow and wherein the buffers used for affinity chromatography on ECH-Lysine SEPHAROSE® 4 Fast Flow resin are the following:
   sodium phosphate 0.05 M, sodium chloride 0.1 M, pH 7.4 for resin equilibration;
   sodium phosphate 0.05 M, sodium chloride 0.1 M pH 7.4 for resin washing;
   sodium phosphate 0.05 M, ε-aminocaproic acid 0.05 M, sodium chloride 0.1 M pH 7.4 for plasminogen elution to obtain a virus inactivated native form plasminogen eluate;
   filtering the virus inactivated native form plasminogen eluate through a 0.22 μm filter to obtain a particulate free virus inactivated native form plasminogen eluate;
   filtering the particulate free virus inactivated native form plasminogen eluate through a dialysis membrane with a 0.1M NaCl solution to remove ε-aminocaproic acid and to obtain a dialyzed virus inactivated native form plasminogen solution;

filtering the dialyzed virus inactivated native form plasminogen solution through a 0.1 µm filter to obtain a second filtrate of virus inactivated native form plasminogen solution; and nanofiltering the second filtrate through a 20 nm filter to obtain pure and virus safe plasminogen (Pg) containing more than 98% wt native form plasminogen (Glu-Pg) suitable to be administered to humans for therapeutic purposes;

wherein no protease inhibitor is employed during said process.

\* \* \* \* \*